(12) United States Patent
Sublett et al.

(10) Patent No.: US 12,147,575 B2
(45) Date of Patent: Nov. 19, 2024

(54) AUTOMATED BATCH DE-IDENTIFICATION OF UNSTRUCTURED HEALTHCARE DOCUMENTS

(71) Applicant: Concord III, LLC, Seattle, WA (US)

(72) Inventors: Andre Sublett, Bainbridge Island, WA (US); Tim Osten, Poulsbo, WA (US); John Scott, Stephenville, TX (US)

(73) Assignee: CONCORD III, LLC, Seattle, WA (US)

( * ) Notice: Subject to any disclaimer, the term of this patent is extended or adjusted under 35 U.S.C. 154(b) by 386 days.

(21) Appl. No.: 17/846,098

(22) Filed: Jun. 22, 2022

(65) Prior Publication Data

US 2023/0418978 A1 Dec. 28, 2023

(51) Int. Cl.
| | |
|---|---|
| *G06F 21/62* | (2013.01) |
| *G06F 40/174* | (2020.01) |
| *G06V 30/10* | (2022.01) |
| *G06V 30/412* | (2022.01) |
| *G16H 10/60* | (2018.01) |

(52) U.S. Cl.
CPC ........ *G06F 21/6254* (2013.01); *G06F 40/174* (2020.01); *G06V 30/10* (2022.01); *G06V 30/412* (2022.01); *G16H 10/60* (2018.01)

(58) Field of Classification Search
CPC ... G06F 21/6254; G06F 40/174; G16H 10/60; G06V 30/10; G06V 30/412
See application file for complete search history.

(56) References Cited

U.S. PATENT DOCUMENTS

| | | | |
|---|---|---|---|
| 2016/0313881 A1* | 10/2016 | Lehoux | G06F 3/0484 |
| 2018/0011974 A1* | 1/2018 | Schneider | G16H 30/20 |
| 2021/0065881 A1* | 3/2021 | Sargent | G16H 30/40 |

* cited by examiner

*Primary Examiner* — Normin Abedin
(74) *Attorney, Agent, or Firm* — CRGO Global; Steven M. Greenberg

(57) ABSTRACT

Batch de-identification of unstructured health care documents includes performing optical character recognition (OCR) upon a form-based document so as to produce an initial set of terms. Amongst the initial set of terms, initial specific terms are identified which contain protected information. Each of the identified initial specific terms are then replaced with synthetically generated corresponding terms. Subsequently, additional OCR is performed upon the form-based document so as to produce a new set of terms and new specific terms are identified amongst the new set of terms which are determined to contain protected information. Finally, the new specific terms are compared to the initial specific terms and the form-based document is then added to a repository of de-identified documents only if none of the new specific terms are equivalent to corresponding ones of the initial specific terms. But otherwise, the form-based document is flagged in error.

15 Claims, 3 Drawing Sheets

AUTOMATED BATCH DE-IDENTIFICATION OF UNSTRUCTURED HEALTHCARE DOCUMENTS

BACKGROUND OF THE INVENTION

Field of the Invention

The present invention relates to the technical field of document processing and more particularly to the de-identification of personally identifiable information in a document.

Description of the Related Art

The exchange of forms-based health care documents amongst health care providers, insurers, patients and the like remains trapped in a universe of heterogeneous and uncoordinated co-dependent computing systems, with different parties to the delivery of health care to a patient providing and receiving health care information according to different standard formats and utilizing different modes of document exchange, ranging from traditional fax to cutting edge wireless device to device transmission. Indeed, owing to the wide disparity in technical sophistication between different actors in the healthcare environment, the fax remains critical as the lingua franca technology of information exchange.

Healthcare information differs from traditional information in that there exists a strict regulatory climate for the security of personal healthcare information (PHI). However, in so far as the use of fax is prevalent in the exchange of healthcare information, using automated text processing methods requires first the conversion of the fax image to text, then the optical character recognition (OCR) of the converted text only then followed by the execution of program logic designed to identify PHI. High speed processing of batches of fax documents, though, does not lend itself well to the simple OCR, parsing and recognition of PHI—especially, when the structure of a received fax representative of a forms-based document is not known a priori.

Modern techniques in high-speed batch processing of fax images address the computationally expensive process of OCR, parsing and recognition through the utilization of machine learning structures trained in the characterization of a format of a forms-based document so that the fields of the document known to have an association with PHI can be rapidly located and the content redacted or replaced from fictitious data so as to ensure compliance with those healthcare privacy regulations affecting the processing of PHI. Of course, in order to train a machine learning structure to properly classify the formatting of a forms-based document, actual forms-based documents must be annotated for ground truth during the training process. The very act, however, of training the machine learning structure, then, can result in an unintentional disclosure of PHI present in the training set of documents. As well, in many instances despite best efforts at reduction, PHI remains at locations not necessarily associated with any type of the PHI.

BRIEF SUMMARY OF THE INVENTION

Embodiments of the present invention address technical deficiencies of the art in respect to the de-identification of large sets of documents for the purpose of training a classifier. To that end, embodiments of the present invention provide for a novel and non-obvious method for the batch de-identification of unstructured health care documents providing a high degree of assurance of the removal of PHI from those document prior to the use of those documents in training a classifier. Embodiments of the present invention also provide for a novel and non-obvious computing device adapted to perform the foregoing method. Finally, embodiments of the present invention provide for a novel and non-obvious data processing system incorporating the foregoing device in order to perform the foregoing method.

In one embodiment of the invention, a method for the batch de-identification of unstructured health care documents includes performing OCR upon a form-based document so as to produce an initial set of terms. Thereafter, amongst the initial set of terms, initial specific terms may be identified which contain PHI. Each of the identified initial specific terms are then replaced with synthetically generated corresponding terms. Subsequently, the method includes an additional OCR process performed upon the form-based document so as to produce a new set of terms and the identification of new specific terms amongst the new set of terms containing PHI. Finally, the new specific terms are compared to the initial specific terms and the form-based document is then added to a repository of de-identified documents only if none of the new specific terms are equivalent to corresponding ones of the initial specific terms. But otherwise, the form-based document is discarded and flagged in error.

In one aspect of the embodiment, the form-based document can be mapped to specify particular fields of the form-based document known to include the PHI, such that the initial specific terms and the new specific terms may be identified at the particular fields in the forms-based document. Further, each of the particular fields can include in the mapping a classification of type. Even further, the synthetically generated corresponding terms for each one of the particular fields are then selected to be consistent with the classification of type for the one of the particular fields. Consequently, the method additionally can include a determination of context for a first one of the particular fields and also a second one of the particular fields, such that the synthetically generated corresponding terms for the first one of the particular fields will be contextually consistent with the determined context for both the first one of the particular fields and the second one of the particular fields.

In another embodiment of the invention, a data processing system can be adapted for batch de-identification of unstructured health care documents. The system includes a host computing platform having one or more computers, each with memory and one or processing units including one or more processing cores. The also includes a batch de-identification module. The module includes computer program instructions enabled while executing in the memory of at least one of the processing units of the host computing platform to OCR a form-based document to produce an initial set of terms, identify initial specific terms amongst the initial set of terms containing PHI and replace in the form-based document each of the identified initial specific terms with synthetically generated corresponding terms.

The program instructions further are enabled to perform additional OCR on the form-based document to produce a new set of terms and identify new specific terms amongst the new set of terms containing protected information. Finally, the program instructions are enabled to compare the new specific terms to the initial specific terms and to add the form-based document to a repository of de-identified documents only if none of the new specific terms are equivalent to corresponding ones of the initial specific terms. Otherwise, the document is discarded and flagged document in error.

In this way, the technical deficiencies of the training a classifier to properly classify the formatting of a forms-based document are overcome owing to the repetitive purging from each document submitted to the training set of PHI and the replacement therewith with information of contextual relevance, while excluding from the training set those of the form-based documents which have been repetitively discovered to contain information likely to include PHI. Indeed, owing to the repetitive processing of each document incorporating information from previous repetitions known to include PHI, PHI may be redacted in a training document even when that PHI is found at an unexpected location in the training document.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the invention provide for batch de-identification of unstructured health care documents. In accordance with an embodiment of the invention, an unstructured forms based document is subjected to OCR and the words produced by OCR are filtered to identify PHI according to identification rules. The words determined to reflect PHI are substituted in the document with synthetically generated, albeit contextually comparable terms according to a replacement table and the document is subjected to an additional OCR. The words produced by the additional OCR are compared to those previously determined to reflect PHI and, to the extent that any matches occur, a flag is raised, but otherwise the document with the substituted synthetically generated terms is added to a table of training data for training a classifier.

Figure 1:
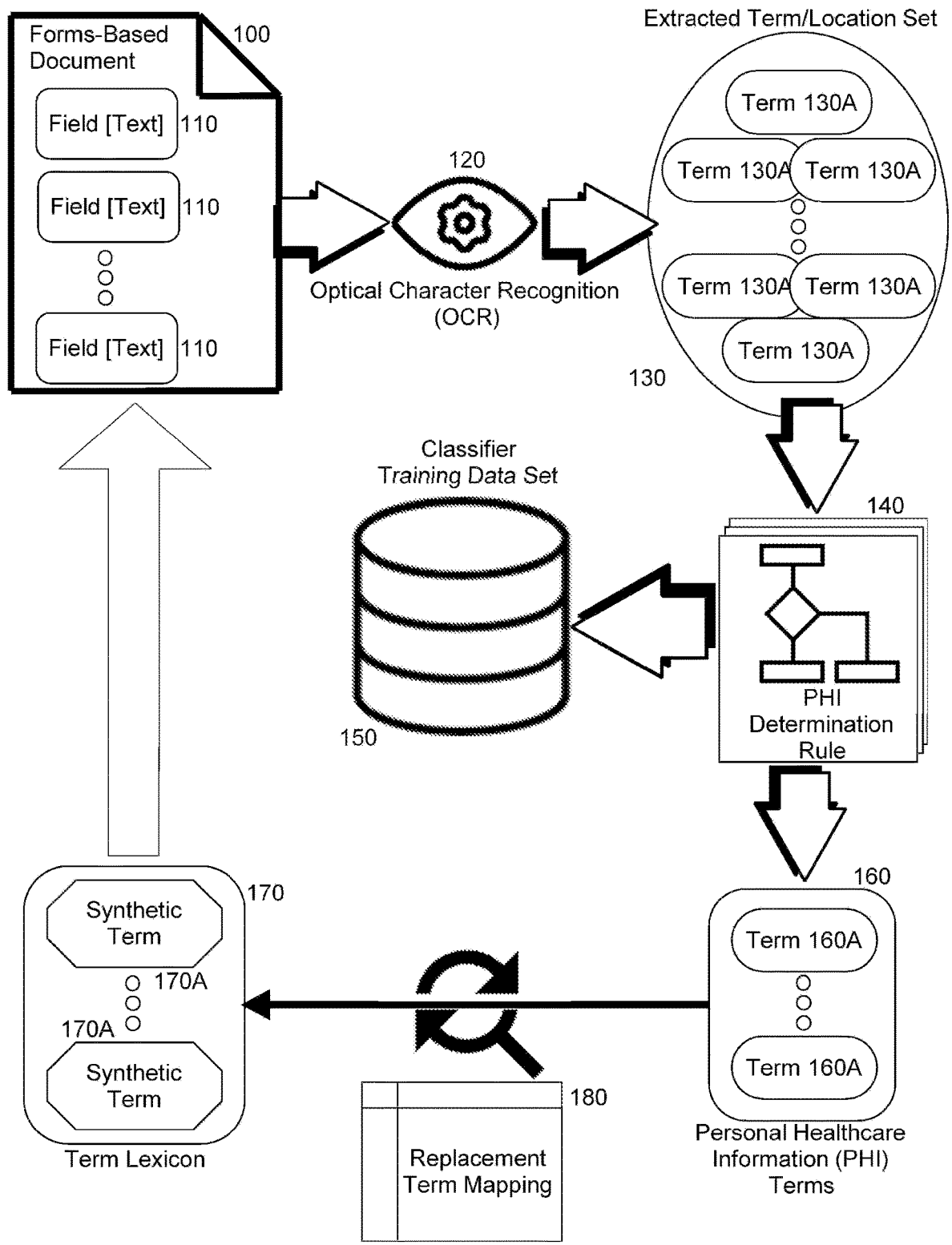
FIG. 1 is a pictorial illustration reflecting different aspects of a process of batch de-identification of unstructured health care documents.

In illustration of one aspect of the embodiment, FIG. 1 pictorially shows a process of batch de-identification of unstructured health care documents. As shown in FIG. 1, a forms-based document 100, unstructured in nature, includes different fields 110 with corresponding textual values. The forms-based document 100 is submitted to OCR 120 in order to produce an extraction set 130 of extracted terms 130A and corresponding locations in the forms-based document 100 from which the extracted terms 130A had been extracted. Each of the extracted terms 130A is then subjected to different PHI determination rules 140 structured to determine if a submitted term contains PHI so that a determination set 160 of PHI terms 160A may be generated. To the extent that the determination set 160 is empty of terms, the document 100 is added to the classifier training data set for use in training a classifier of document images.

To the extent, however, the determination set 160 is not empty and includes PHI terms 160A, a substitute set 170 of corresponding synthetic terms 170A is generated according to a replacement term mapping 180 which maps PHI terms 160A to de-identified, replacements of contextual sameness. In this regard, names can be replaced with random names, addresses with random addresses, medical conditions replaced with random conditions and the like, but the choice of replacement terms is based upon the context of each one of the PHI terms 160A to be replaced so that gender specific names amongst the PHI terms 160A are replaced with the names of the same gender, addressing information amongst the PHI terms 160A of particular region are replaced with addressing information of the same region, and so forth.

Each of the PHI terms 160 in the determination set 160 are then redacted at the location in the forms-based document 100 from which the PHI terms 160 had been extracted and replaced therein with a correspondingly mapped one of the synthetic terms 170A. The updated form of the forms-based document 100 is then re-submitted to OCR 120. Subsequent to re-submission, once again extracted terms 130A are received in an extraction set 130 and subjected to the PHI determination rules 140. In the event that the resulting determination set 160 is null, the forms-based document 100 is added to the classifier training data set 150 inclusive of the synthetic terms 170A in place of the previously extracted PHI terms 160A. Otherwise, the forms-based document 100 is discarded and flagged in error. Optionally, the process can repeat once again and the process can continue through a time out condition, an excessive try condition, or until no PHI terms 160 are found in the extraction set 160.

Figure 2:
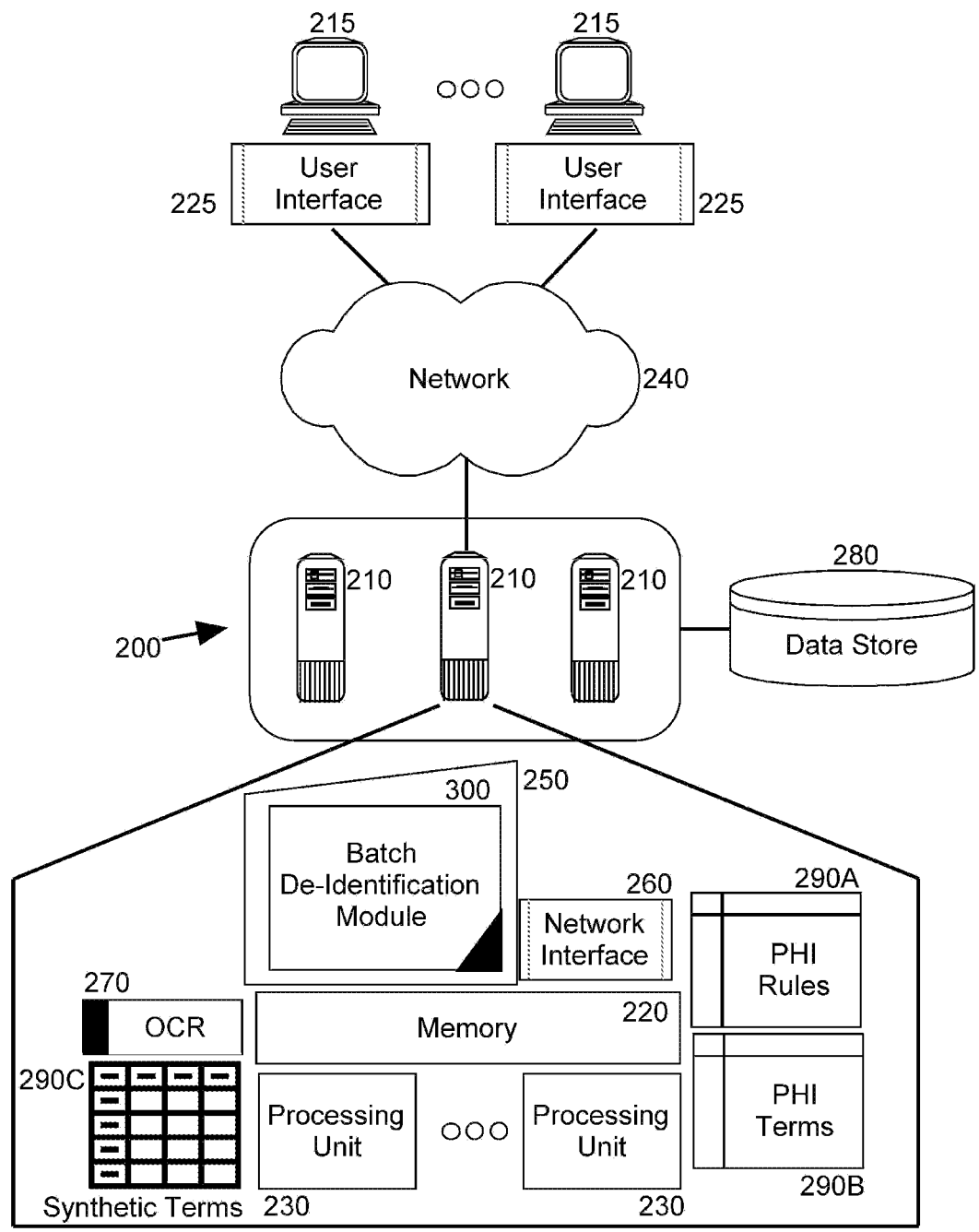
FIG. 2 is a block diagram depicting a data processing system adapted to perform one of the aspects of the process of FIG. 1; and, FIG. 3 is a flow chart illustrating one of the aspects of the process of FIG. 1.

Aspects of the process described in connection with FIG. 1 can be implemented within a data processing system. In further illustration, FIG. 2 schematically shows a data processing system adapted to perform batch de-identification of unstructured health care documents. In the data processing system illustrated in FIG. 1, a host computing platform 200 is provided. The host computing platform 200 includes one or more computers 210, each with memory 220 and one or more processing units 230. The computers 210 of the host computing platform (only a single computer shown for the purpose of illustrative simplicity) can be co-located within one another and in communication with one another over a local area network, or over a data communications bus, or the computers can be remotely disposed from one another and in communication with one another through network interface 260 over a data communications network 240. As well, a data store 280 for persistently storing data is communicatively coupled to the host computing platform either directly or from over the data communications network 240.

Notably, a computing device 250 including a non-transitory computer readable storage medium can be included with the data processing system 200 and accessed by the processing units 230 of one or more of the computers 210.

The computing device stores 250 thereon or retains therein a program module 300 that includes computer program instructions which when executed by one or more of the processing units 230, performs a programmatically executable process for batch de-identification of unstructured health care documents. Specifically, the program instructions during execution process a batch of unstructured form-based documents in the memory 220 first, by invoking for each of the documents, OCR logic 270 so as to produce in the memory 220, a set of terms to which different PHI rules 290A in the memory 220 are applied in order to reduce the set of terms to only PHI terms 290B. For example, the PHI rules 290A correlate identifiable fields in the forms based document previously known to be associated with PHI and extract in connection with those fields, associated values as the PHI terms 290B.

The program instructions then replace the PHI terms 290B in the document with synthetic terms 290C and submit the document with synthetic terms 290C to the OCR logic 270 to produce a new set of terms to which the PHI rules 290A are applied. To the extent that the PHI rules 290A fail to produce additional PHI terms 290B evident in the document, the program instructions then add the document to the data store 280 as a training document for a classifier, but otherwise the program instructions flag the document as an error. Alternatively, the program instructions can repeat the foregoing process of replacing each of the located PHI terms 290B with the synthetic terms 290C in the document and re-submitting the document to the OCR logic 270 until no further PHI terms 290B are identified in the re-submitted document.

Importantly, the program instructions select each one of the synthetic terms 290C to replace a corresponding one of the PHI terms 290B in accordance with a context determined for the corresponding one of the PHI terms 290B. For instance, the context of the corresponding one of the PHI terms 290B can be set forth explicitly in the document with a label or annotation, or the context of the corresponding one of the PHI terms 290B can be inferred based upon a location of the corresponding one of the PHI terms 290B in the document. In the latter instance, the context can be inferred based upon the location of the corresponding one of the PHI terms 290B relative to another one of the PHI terms 290B in the document. As well, the context can be inferred based upon a combination of the PHI terms 290B such as last name and city of residence, or city of residence and medication, or weight and city of residence, to name only a few examples. The context once determined can be provided for the corresponding one of the PHI terms 290B as a key to a table of the synthetic terms 290C along with the type of the corresponding one of the PHI terms 290B in order to retrieve a contextually relevant one of the synthetic terms 290C to replace the corresponding one of the PHI terms 290B in the document.

Figure 3:
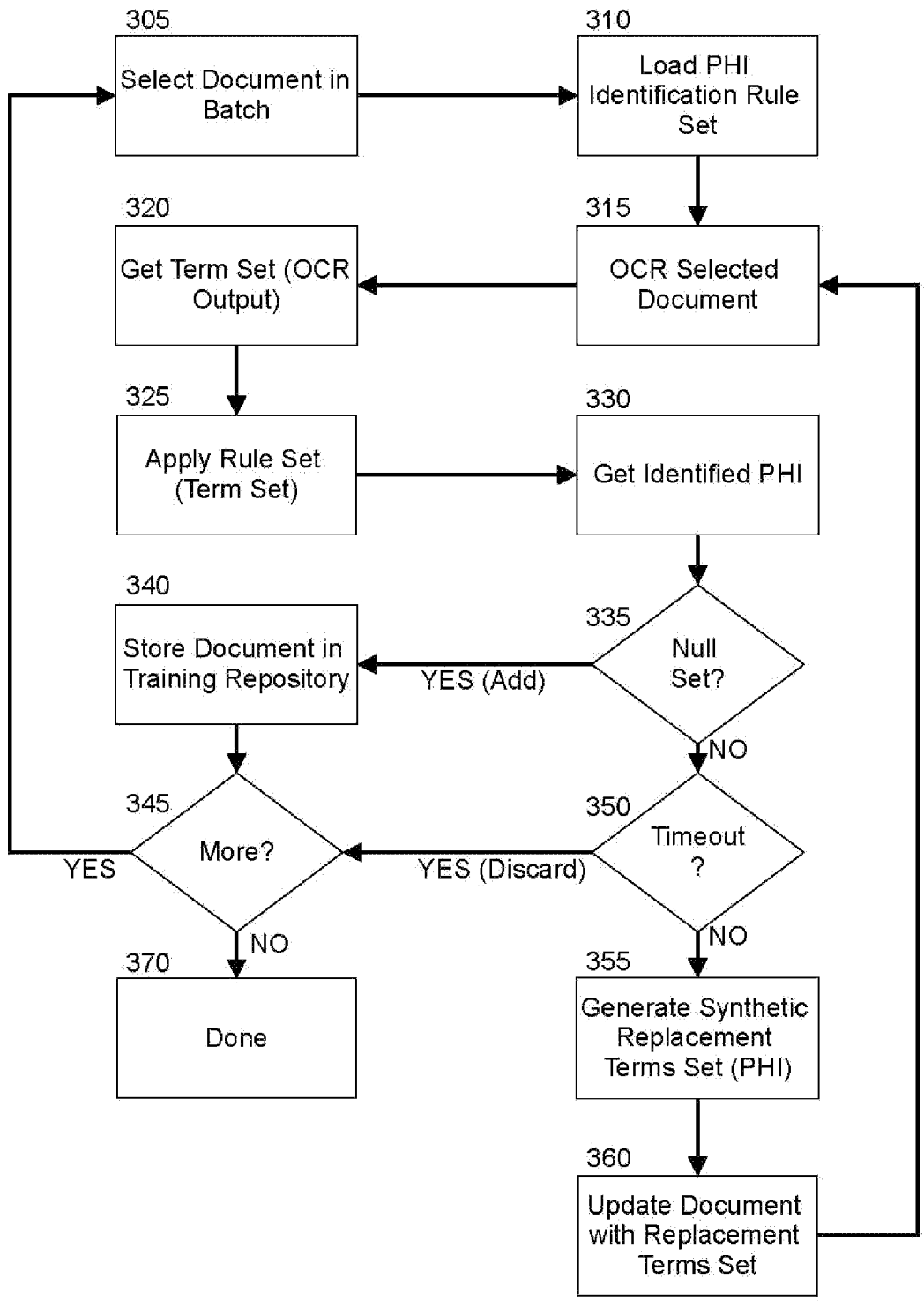

In further illustration of an exemplary operation of the module, FIG. 3 is a flow chart illustrating one of the aspects of the process of FIG. 1. Beginning in block 305, a first document can be selected from a batch of non-structured forms-based documents queued for processing into a training data set for training a classifier classifying documents according to field location. In block 310, a set of rules can be loaded, each rule determining when PHI is present in connection with a field of a form. In block 315, the document is submitted for OCR and in block 320, an output set of terms is received from the OCR. In block 325, the PHI rule set is applied to each of the terms in the output set in order to determine whether or not PHI is present in the document. In block 330, the identified PHI terms are grouped in a set.

In decision block 335, it is determined whether or not the set contains one or more PHI terms. If not, the document can be presumed not to include PHI and the document can be added to the training repository for use as a training input to the classifier in block 340. On the other hand, if it is determined in decision block 335 that the set contains one or more PHI terms, it can be determined if a timeout condition (or an excessive tries condition) has arisen. If not, in block 355 a set of synthetic replacement terms are determined in correspondence to the PHI terms in the set. Then, in block 360 the document is updated with the synthetic replacement terms such that each PHI term in the set is removed at the location of the PHI term in the document and replaced with a corresponding one of the synthetic replacement terms. Subsequently, the document with replaced synthetic replacement terms is returned to the OCR step of block 315.

As each document in the batch is determined to be devoid of PHI terms in decision block 335 so that the documents are added to the repository, in decision block 345 it is determined if additional documents in the batch remain to be considered. If so, the process returns to block 305 at which a next document in the batch is selected for consideration. But, in decision block 345, when no further documents remain to be processed, the methodology ends in block 370.

Of import, the foregoing flowchart and block diagram referred to herein illustrate the architecture, functionality, and operation of possible implementations of systems, methods, and computing devices according to various embodiments of the present invention. In this regard, each block in the flowchart or block diagrams may represent a module, segment, or portion of instructions, which includes one or more executable instructions for implementing the specified logical function or functions. In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

More specifically, the present invention may be embodied as a programmatically executable process. As well, the present invention may be embodied within a computing device upon which programmatic instructions are stored and from which the programmatic instructions are enabled to be loaded into memory of a data processing system and executed therefrom in order to perform the foregoing programmatically executable process. Even further, the present invention may be embodied within a data processing system adapted to load the programmatic instructions from a computing device and to then execute the programmatic instructions in order to perform the foregoing programmatically executable process.

To that end, the computing device is a non-transitory computer readable storage medium or media retaining therein or storing thereon computer readable program instructions. These instructions, when executed from memory by one or more processing units of a data processing system, cause the processing units to perform different programmatic processes exemplary of different aspects of the programmatically executable process. In this regard, the processing units each include an instruction execution device such as a central processing unit or "CPU" of a computer. One or more computers may be included within the data processing system. Of note, while the CPU can be a single core CPU, it will be understood that multiple CPU cores can operate within the CPU and in either instance, the instructions are directly loaded from memory into one or more of the cores of one or more of the CPUs for execution.

Aside from the direct loading of the instructions from memory for execution by one or more cores of a CPU or multiple CPUs, the computer readable program instructions described herein alternatively can be retrieved from over a computer communications network into the memory of a computer of the data processing system for execution therein. As well, only a portion of the program instructions may be retrieved into the memory from over the computer communications network, while other portions may be loaded from persistent storage of the computer. Even further, only a portion of the program instructions may execute by one or more processing cores of one or more CPUs of one of the computers of the data processing system, while other portions may cooperatively execute within a different computer of the data processing system that is either co-located with the computer or positioned remotely from the computer over the computer communications network with results of the computing by both computers shared therebetween.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

We claim:

1. A method for the batch de-identification of unstructured health care documents, the method comprising:
   optical character recognizing a form-based document, the optical character recognition (OCR) producing an initial set of terms;
   identifying initial specific terms amongst the initial set of terms containing protected information and replacing in the form-based document each of the identified initial specific terms with synthetically generated corresponding terms;
   performing additional OCR on the form-based document to produce a new set of terms and identifying new specific terms amongst the new set of terms containing protected information;
   comparing the new specific terms to the initial specific terms; and,
   adding the form-based document to a repository of de-identified documents only if none of the new specific terms are equivalent to corresponding ones of the initial specific terms, but otherwise flagging the form-based document in error.

2. The method of claim 1, further comprising:
   mapping the form-based document to specify particular fields of the form-based document known to include the protected information; and,
   identifying the initial specific terms and the new specific terms at the particular fields.

3. The method of claim 2, wherein each of the particular fields includes in the mapping a classification of type.

4. The method of claim 3, wherein the synthetically generated corresponding terms for each one of the particular fields are consistent with the classification of type for the one of the particular fields.

5. The method of claim 1, further comprising, determining a context for a first one of the particular fields and also a second one of the particular fields, wherein the synthetically generated corresponding terms for the first one of the particular fields is contextually consistent with the determined context for both the first one of the particular fields and the second one of the particular fields.

6. The device of claim 1, wherein the method further comprises:
   mapping the form-based document to specify particular fields of the form-based document known to include the protected information; and,
   identifying the initial specific terms and the new specific terms at the particular fields.

7. The device of claim 6, wherein each of the particular fields includes in the mapping a classification of type.

8. The device of claim 7, wherein the synthetically generated corresponding terms for each one of the particular fields are consistent with the classification of type for the one of the particular fields.

9. A data processing system adapted for batch de-identification of unstructured health care documents, the system comprising:
   a host computing platform comprising one or more computers, each with memory and one or processing units including one or more processing cores; and,
   a batch de-identification module comprising computer program instructions enabled while executing in the memory of at least one of the processing units of the host computing platform to perform:
      optical character recognizing a form-based document, the optical character recognition (OCR) producing an initial set of terms;
      identifying initial specific terms amongst the initial set of terms containing protected information and replacing in the form-based document each of the identified initial specific terms with synthetically generated corresponding terms;
      performing additional OCR on the form-based document to produce a new set of terms and identifying new specific terms amongst the new set of terms containing protected information;
      comparing the new specific terms to the initial specific terms; and,
      adding the form-based document to a repository of de-identified documents only if none of the new specific terms are equivalent to corresponding ones of the initial specific terms, but otherwise flagging the form-based document in error.

10. The system of claim 9, wherein the program instructions are further enabled to perform:
- mapping the form-based document to specify particular fields of the form-based document known to include the protected information; and,
- identifying the initial specific terms and the new specific terms at the particular fields.

11. The system of claim 10, wherein each of the particular fields includes in the mapping a classification of type.

12. The system of claim 11, wherein the synthetically generated corresponding terms for each one of the particular fields are consistent with the classification of type for the one of the particular fields.

13. The system of claim 10, wherein the program instructions are further enabled to perform:
- determining a context for a first one of the particular fields and also a second one of the particular fields, wherein the synthetically generated corresponding terms for the first one of the particular fields is contextually consistent with the determined context for both the first one of the particular fields and the second one of the particular fields.

14. A computing device comprising a non-transitory computer readable storage medium having program instructions stored therein, the instructions being executable by at least one processing core of a processing unit to cause the processing unit to perform a method for batch de-identification of unstructured health care documents, the method including:
- optical character recognizing a form-based document, the optical character recognition (OCR) producing an initial set of terms;
- identifying initial specific terms amongst the initial set of terms containing protected information and replacing in the form-based document each of the identified initial specific terms with synthetically generated corresponding terms;
- performing additional OCR on the form-based document to produce a new set of terms and identifying new specific terms amongst the new set of terms containing protected information;
- comparing the new specific terms to the initial specific terms; and,
- adding the form-based document to a repository of de-identified documents only if none of the new specific terms are equivalent to corresponding ones of the initial specific terms, but otherwise flagging the form-based document in error.

15. The device of claim 14, wherein the method further comprises determining a context for a first one of the particular fields and also a second one of the particular fields, wherein the synthetically generated corresponding terms for the first one of the particular fields is contextually consistent with the determined context for both the first one of the particular fields and the second one of the particular fields.

* * * * *